United States Patent
Gibbs et al.

(10) Patent No.: US 7,452,506 B2
(45) Date of Patent: Nov. 18, 2008

(54) AUTOMATED STAINING AND DECOLORIZATION OF BIOLOGICAL MATERIAL

(75) Inventors: Walden Lewis Gibbs, Wichita Falls, TX (US); Jeffrey Dwight Gibbs, Iowa Park, TX (US)

(73) Assignee: Burns Energy Company, Inc., Wichita Falls, TX (US)

( * ) Notice: Subject to any disclaimer, the term of this patent is extended or adjusted under 35 U.S.C. 154(b) by 483 days.

(21) Appl. No.: 10/274,613

(22) Filed: Oct. 21, 2002

(65) Prior Publication Data

US 2003/0138877 A1 Jul. 24, 2003

Related U.S. Application Data

(62) Division of application No. 09/469,557, filed on Dec. 22, 1999, now Pat. No. 6,468,764.

(60) Provisional application No. 60/116,485, filed on Jan. 20, 1999.

(51) Int. Cl.
*G01N 1/31* (2006.01)
*G01N 1/30* (2006.01)

(52) U.S. Cl. ............... 422/82.05; 422/68.1; 435/40.5

(58) Field of Classification Search ............... 435/4, 435/40.5, 40.51, 808; 382/133; 422/68.1, 422/82.05

See application file for complete search history.

(56) References Cited

U.S. PATENT DOCUMENTS

| | | | |
|---|---|---|---|
| 3,837,795 A * | 9/1974 | Becker et al. | 436/46 |
| 4,029,470 A * | 6/1977 | Wilkins et al. | 8/94.11 |
| 4,639,421 A | 1/1987 | Sage | |
| 4,665,024 A | 5/1987 | Mansour | |
| 5,081,017 A | 1/1992 | Longoria | |
| 5,137,810 A | 8/1992 | Sizemore et al. | |
| 5,340,719 A | 8/1994 | Hajek et al. | |
| 5,424,826 A * | 6/1995 | Kinney | 356/326 |
| 5,449,622 A * | 9/1995 | Yabe et al. | 436/63 |
| 5,545,535 A | 8/1996 | Roth et al. | |
| 5,554,505 A | 9/1996 | Hajek et al. | |
| 5,593,886 A | 1/1997 | Gaddy | |
| 5,610,198 A * | 3/1997 | Barry et al. | 514/712 |
| 5,633,722 A * | 5/1997 | Wasinger et al. | |
| 5,827,680 A * | 10/1998 | Meszaros et al. | 435/34 |
| 6,056,790 A * | 5/2000 | Clark et al. | 8/502 |

OTHER PUBLICATIONS

Joklik et al., Zinsser Microbiology, 18th edition (1984), pp. 19-20. Prentice-Hall, Inc., USA.*

* cited by examiner

*Primary Examiner*—Jill Warden
*Assistant Examiner*—Paul S Hyun
(74) *Attorney, Agent, or Firm*—Mark D. Perdue

(57) ABSTRACT

An improved method and apparatus for staining samples of biological material for accurate analysis of the sample. Biological material is applied to a substrate, such as a microscope slide. The biological specimen is then stained with a selected staining composition, which may be gentian violet for a Gram's Stain analysis. The stained biological material is at least partially decolorized and the level of decolorization is analyzed optically. If necessary, the decolorizing step and the optical analysis steps are repeated until a selected level of decolorization is obtained.

13 Claims, 4 Drawing Sheets

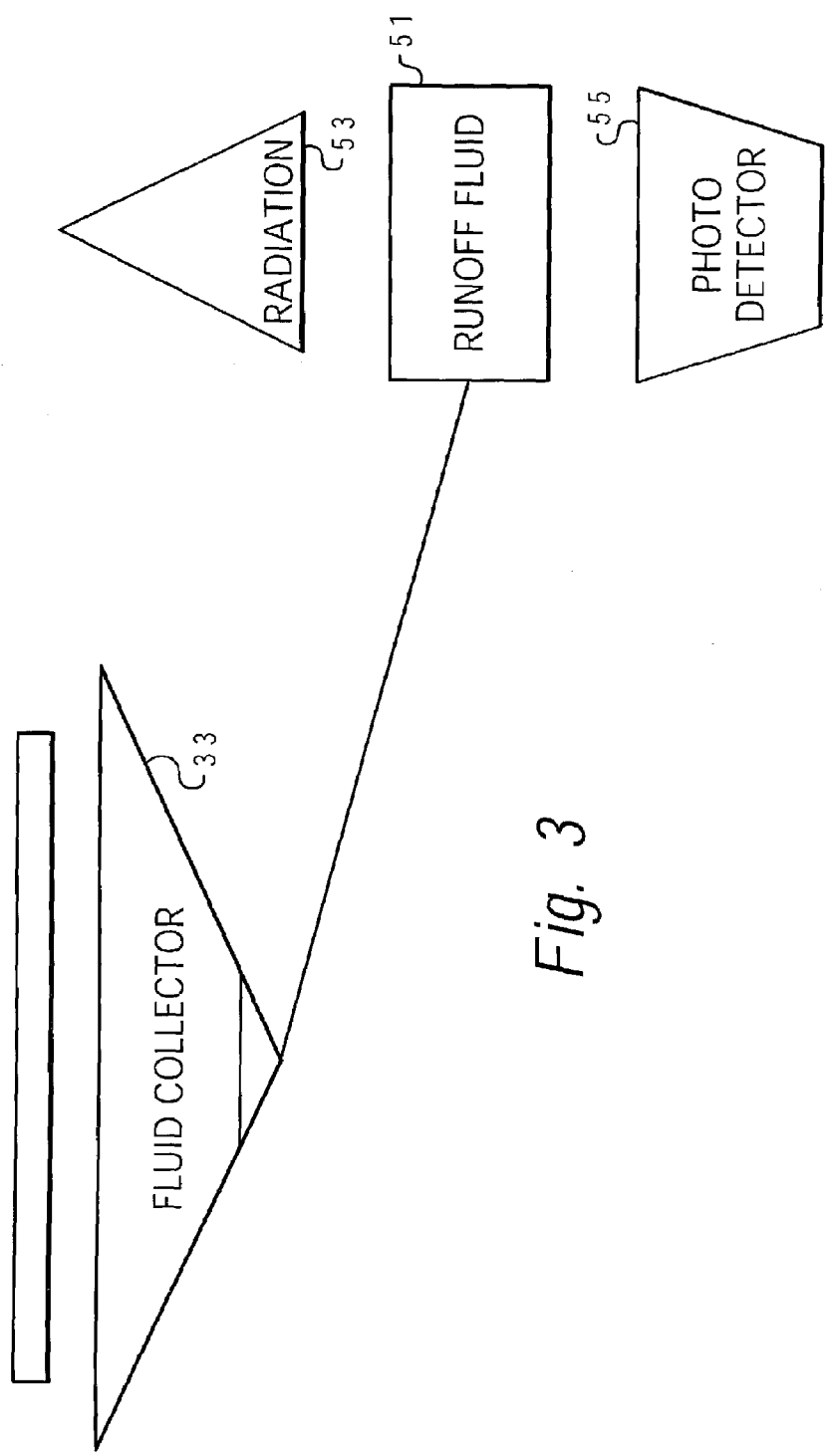

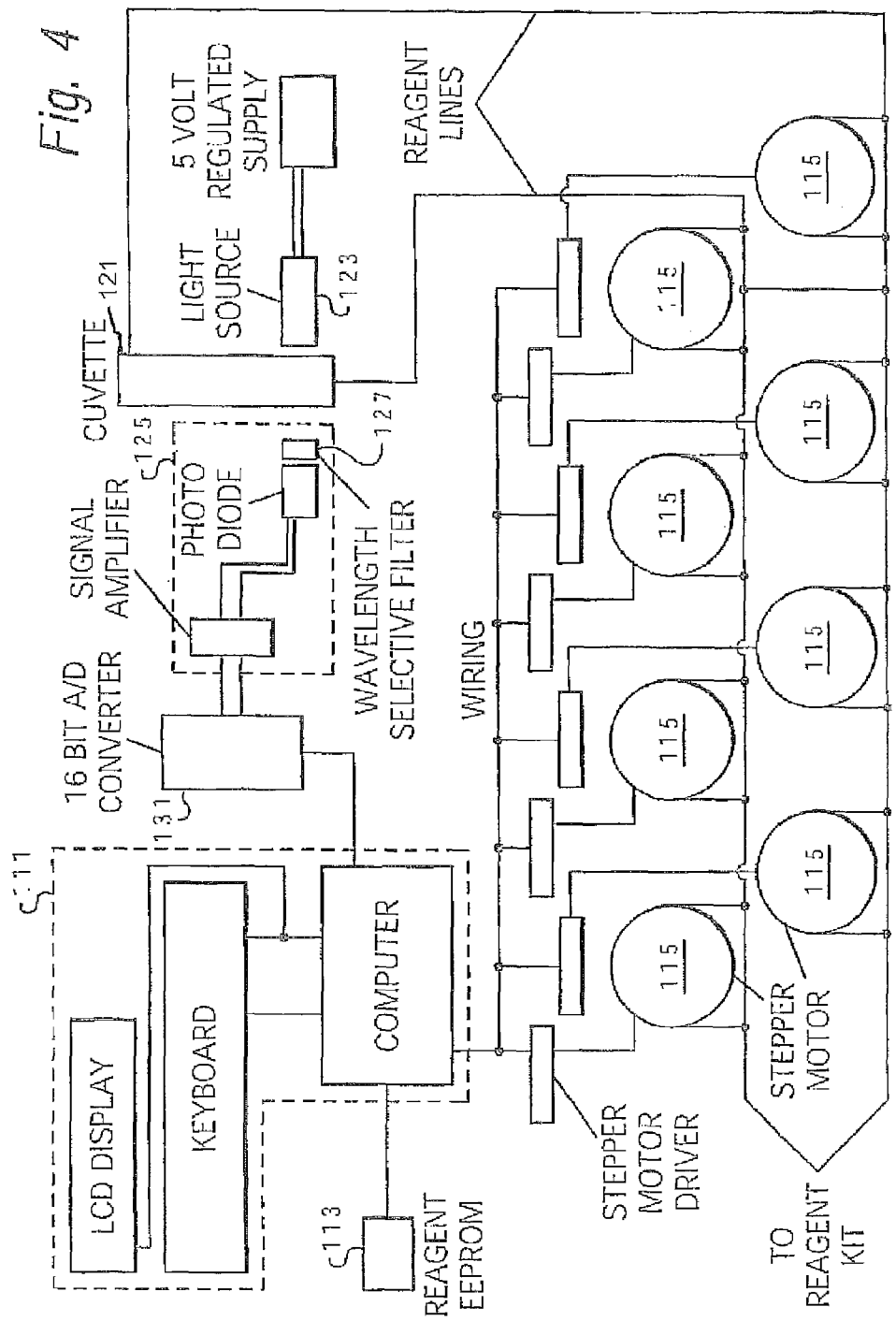

AUTOMATED STAINING AND DECOLORIZATION OF BIOLOGICAL MATERIAL

CROSS REFERENCE TO RELATED APPLICATION

This application is a divisional application of Ser. No. 09/469,557, filed on Dec. 22, 1999, now U.S. Pat. No. 6,468,764.

This application claims priority from U.S. Provisional Application Ser. No. 60/116,485, filed Jan. 20, 1999, entitled AUTOMATED STAINING AND DECOLORIZATION OF BIOLOGICAL MATERIAL.

BACKGROUND OF THE INVENTION

1. Field of the Invention

The present invention relates generally to methods and apparatus for the diagnostic staining of biological material. More particularly, the present invention relates to methods and apparatus for staining biological material on microscope slides in an automated fashion.

2. Background and Summary of Prior Art

Biological material, whether viruses, bacteria, or various smears or samples of blood, mucus, and the like, have been analyzed for centuries, since Van Leeuvenhoek invented the microscope. Typically the sample of material is applied to a microscope slide, stained or otherwise rendered into an analyzable state, and analyzed by a human technician or scientist.

As laboratory services for hospitals, physician's offices, veterinarians, and other life-science-based enterprises become increasingly "outsourced," the laboratory's ability to analyze slides of biological material rapidly and accurately becomes increasingly important. Several steps have been made toward automating these processes, but it seems unlikely that the skilled human technician will be almost entirely removed from the process in the foreseeable future.

A fairly typical and important laboratory staining technique is known as Gram's Stain, which was devised by H. C. J. Gram. The Gram's Stain is a "gateway" test that indicates to the technician the presence (or absence) of certain bacteria in a sample of biological material and gives the technician or scientist information necessary or helpful to make further analysis. For instance, Gram's Stain can be used to determine which pathogens are suspected and lead to an antibiotic prescription until further identification can be conducted.

Like several staining or analysis methods, Gram's Stain involves treating the biological material, usually applied to a conventional microscope slide, with a number of reagents or stains. The reagents or stains emphasize or highlight the presence (or absence) of certain types or features of bacteria or other biological material that is helpful to the technician. In the Gram's Stain, the bacteria are treated first with gentian violet, and then with a formulation of iodine conventionally known as Gram's iodine. This stains almost all of the bacteria a deep blue or violet. "Gram positive" bacteria absorb the gentian violet and Gram's iodine into their cellular structure, while "Gram negative" bacteria are stained only superficially. The sample is then washed with acid alcohol, which "decolorizes" or washes the color from Gram negative bacteria. Thus, when adequate decolorization has occurred, the blue or violet Gram positive bacteria can be distinguished from the colorless (or less deeply blue or violet) Gram negative bacteria. A "counter-stain," of fuchsine for example, may be applied to turn the blue or violet bacteria to a reddish shade to improve their visibility. Decolorization is critical to the Gram's Stain because too little decolorization can yield false Gram positives and too much decolorization can yield false Gram negatives.

Several past attempts at providing automating the slide preparation and staining process have met with limited success. For example, U.S. Pat. No. 4,029,470, Jun. 14, 1977 to Wilkins et al. provides an apparatus for automatically staining a single microscope slide without a lab technician touching the slide. This patent addresses the decolorization issue by timing the application of decolorizing agent in selected volume. The time/volume control of decolorization is insufficient to accurately decolorize a Gram Stain. The decolorization process is simply too dependent upon observation and manual work to be so easily controlled.

GG&B Company of Wichita Falls, Tex., sells a more sophisticated slide stainer under the registered trademark Quick Slide®. This device fully automates the preparation of slides for analysis and is a useful tool in the modern medical laboratory. Nevertheless, the Quick Slide® device is not capable of accurately decolorizing slides for a staining process such as the Gram's Stain.

U.S. Pat. Nos. 5,545,535; 4,665,024; and 4,639,421 all disclose flourescent gram stains and methods of analyzing bacteria stained with the flourescent dyes in which a spectral analysis of the fluorescence of the stained bacteria is used to analyze the Gram positive and negative bacteria in the sample. These inventions do not address the decolorization issue because it seems that decolorization is less important (or unimportant) where flourescent dyes or stains are used in lieu of the conventional Gram's Stain of gentian violet.

A need exists, therefore, for an automated method and apparatus for staining biological material and accurately decolorizing the stained sample prior to analysis.

SUMMARY OF THE INVENTION

It is a general object of the present invention to provide an improved method and apparatus for staining samples of biological material for accurate analysis of the sample. These and other objects of the invention are achieved by applying the biological material to a substrate, preferably a microscope slide. The biological material is then stained with a selected staining composition, which may be gentian violet for a Gram's Stain analysis. The stained biological material is at least partially decolorized and the level of decolorization is analyzed optically. If necessary, the decolorizing step and the optical analysis steps are repeated until a selected level of decolorization is obtained.

Other objects, features, and advantages of the present invention will become apparent with reference to the drawings and description, which follow.

BRIEF DESCRIPTION OF THE DRAWINGS

FIG. 3 is a schematic depiction of the decolorization analysis module of the apparatus of FIG. 1.

FIG. 4 is a more detailed schematic description of an apparatus for staining biological materials according to the present invention.

DETAILED DESCRIPTION OF THE INVENTION

Figure 1:
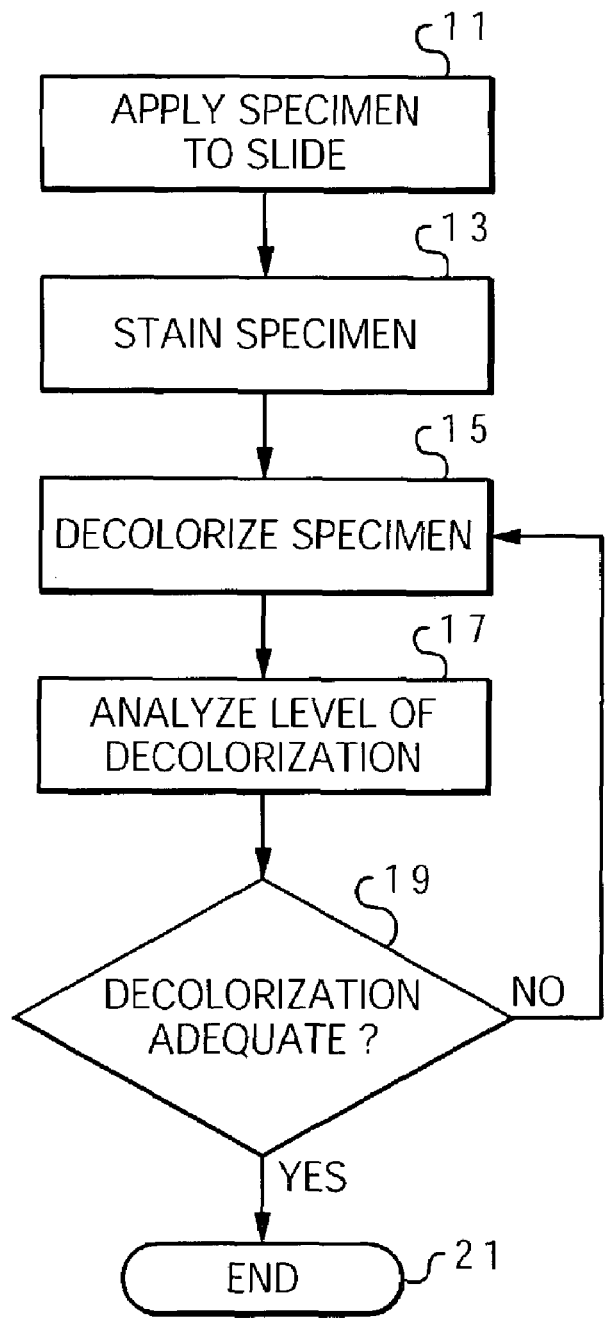
FIG. 1 is a schematic depiction of the apparatus according to the present invention.

Referring now to the figures, and particularly to FIG. 1, a high-level flowchart depicts the steps of the method or process according to the present invention. At block 11, a sample of biological material is applied to the substrate, typically a conventional microscope slide, to create a specimen. The biological specimen can be affixed or applied in a number of conventional ways, which depend largely on preference and subsequent processing. The biological specimen may include blood, mucus, tissue samples, or the like, and is obtained in conventional ways.

At step 13, the biological specimen is stained or dyed according to the analytical process to be employed. For the Gram Stain, the dye or stain is crystal or gentian violet in combination with Gram's iodine. The stain or dye stains the components of the biological specimen, in some cases only superficially; in others, the dye is absorbed within the cell structure.

At step 15, the biological specimen is decolorized, that is, the dye or stain that is not absorbed within the cell structure, but only superficially, is washed away. For the Gram Stain, the decolorization is accomplished by washing the specimen with acid alcohol (alcohol treated to be slightly acidic). The washing may be controlled by volume of fluid applied and time of application to yield a very rough measure of the level of decolorization achieved in this step.

At step 17, the level of decolorization is measured or analyzed. The specific method of analysis employed is discussed in greater detail with reference to FIG. 3. Generally, the method applies radiation (visible spectrum, infrared, ultraviolet) to the "run-off" fluid or material resulting from application of acid alcohol to the specimen. The radiation passes through the acid alcohol, which itself is stained with gentian violet, Gram's iodine, and a safrin counter-stain. Because the run-off fluid is stained, it absorbs certain wavelengths or frequencies of the radiation and transmits others. The radiation transmitted through the run-off fluid is measured and compared to a threshold value. The threshold value is empirically determined based upon the characteristics of the staining and decolorization process used (e.g. dye or stain characteristics and composition and decolorizing agent characteristics and composition).

At step 19, the comparison is analyzed to determine if the desired or selected level of decolorization has occurred. If so, the process ends, at step 21, and the slide is ready for further processing or analysis. If the level of decolorization is inadequate, more washing with decolorant occurs, as well as the analysis of step 17, until the sample is adequately decolorized.

Figure 2:
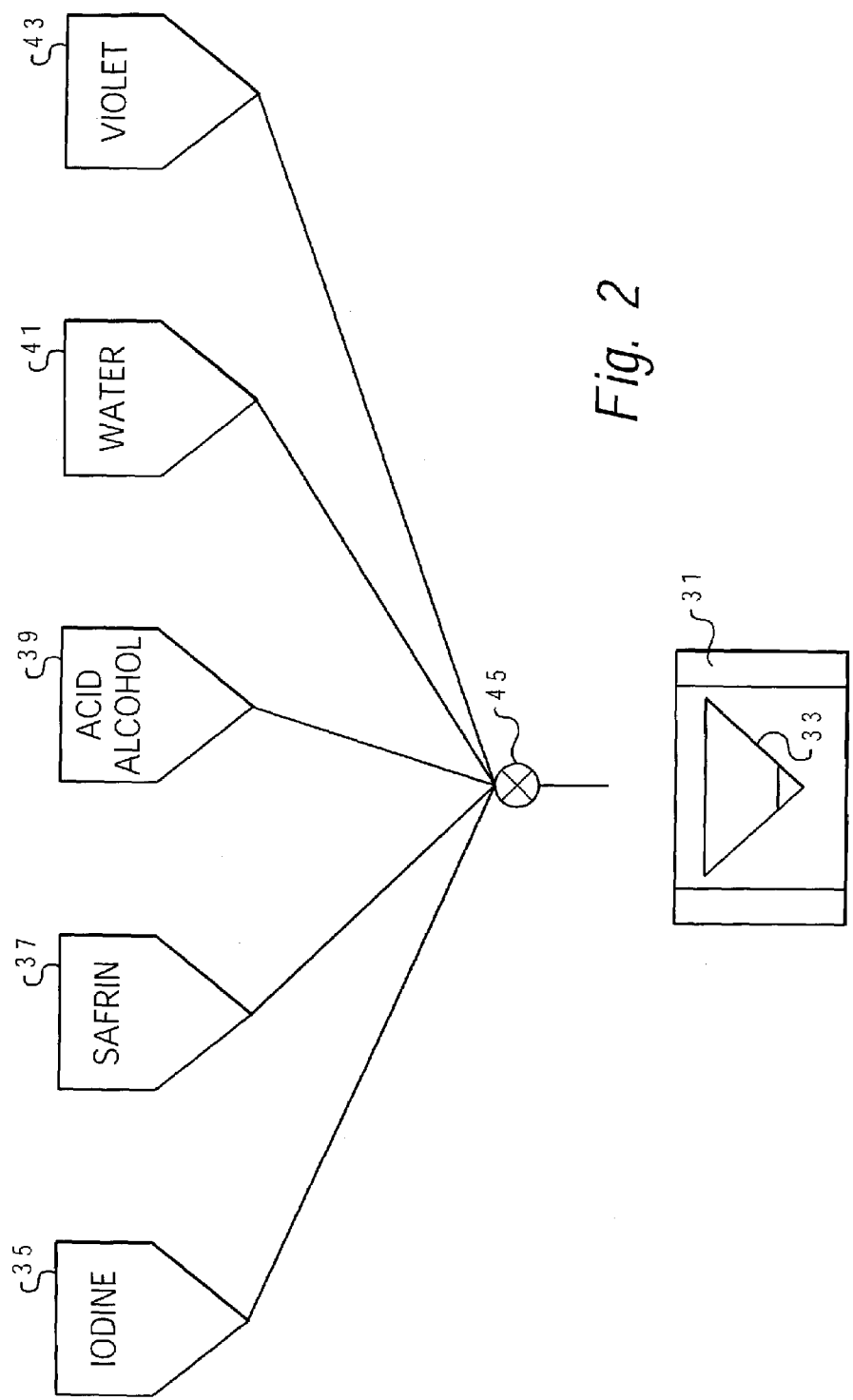
FIG. 2 is a high-level flow chart of the method according to the present invention.

FIG. 2 is a schematic depiction of the apparatus employing the process of FIG. 1. The apparatus comprises a slide carrier or mount 31 on which the microscope slide or other specimen substrate is placed or carried. A collector 33 is provided to collect or catch process fluids as they run off the slide. The apparatus is also provided with five reservoirs, 35, 37, 39, 41, 43 for the process fluids, which, for the Gram Stain process, include crystal or gentian violet, Gram's iodine, safrin (counter-stain), acid alcohol, and water. These reservoirs are connected to a fluid handling and metering system 45 that washes the biological specimen with the appropriate fluid in the appropriate amount. Time- and volume-controlled application of the staining fluids (violet, iodine, and safrin) is adequate for those fluids to perform their function. As previously discussed, time and volume control of the decolorization process, alone, is not adequate.

FIG. 3 is a schematic representation of the "decolorization module" of the apparatus of FIG. 2. The decolorization module can be manufactured as part of the slide carrier or mount (31 in FIG. 2), or can be a physically separate portion of the apparatus. The run-off fluid from the decolorization process, which includes acid alcohol, either diluted with water or not, is collected by collector 33. The run-off from the decolorization step is collected in a chamber 51, which is preferably optically transparent. In addition to chamber 51, the decolorization module includes a source of radiation 53 arranged and located to irradiate the fluid contents of chamber 51 with radiation of a selected wavelength or combination of wavelengths.

The run-off fluid, being stained, will transmit certain wavelengths of radiation and absorb others. The radiation transmitted through chamber 51 and run-off fluid impinges on a photo detector 55. Photo detector 55 and associated electrical circuitry, including filters and the like, generates an electrical signal whose strength is proportional to the intensity and wavelength of the radiation impinging on detector 55. This signal is input to a comparator or similar device capable of comparing the signal to a pre-determined threshold value representative of adequate decolorization. If the signal compares favorably with the threshold value, the user is alerted and the stained slide is indicated to be ready for visual analysis. If the measured level of decolorization indicates that decolorization is inadequate, the specimen can be washed again and the run-off fluid analyzed as set forth above.

The transmissibility of radiation through the run-off fluid is a function of the level of decolorization of the specimen on the slide. Thus, the level of decolorization can be empirically determined to correspond to a threshold value of transmitted radiation detected by photo detector 55. Thus, the proper level of decolorization is optically detected without human interference or involvement, which permits accurate, automated slide staining to a degree not previously available.

FIG. 4 is a more detailed schematic of the apparatus according to the present invention. Central to the apparatus is the control system residing on a personal computer (PC) 111, which may be a PC dedicated for use with the invention, or a conventional PC with control software resident on the hard drive and RAM, for use with the invention as needed. The other components, which may be external to the PC, are housed within an enclosure (not shown) that is coupled to the PC.

The enclosure includes reservoirs (not shown) for the process fluids, which include, for Gram staining, gentian violet, Gram's iodine, distilled water, safrin, and acid alcohol. Other fluids may be appropriate for other staining processes. An EEPROM 113, programmed appropriately, is coupled to the computer through an IEEE 488 interface, and also to a series of stepper motors 115. Together, EEPROM 113 and stepper motors 115 control the flow of process fluids from the reservoirs, through fluid passages, to the microscope slide. The run-off of decolorization fluid (acid alcohol), is captured temporarily in a glass cuvette 121. EEPROM 113 is an appropriately programmed Bell-Milgray 93LC46/P. Stepper motors 115 and their associated controllers are Oriental Motors Model PK264-01A, and Newark NDN2878U, respectively.

Adjacent the microscope slide, a regulated power supply powers a light source 123, which is a Gilway 5-Volt, 775-Ampere technical lamp. This is the radiation source and is arranged to direct visible-spectrum radiation through the cuvette 121 and its contents. A Digi-Key OPT202P-ND photodiode 125 with an on-chip amplifier is arranged on the side of cuvette 121 opposite the lamp. A wavelength-selective filter 127, Omega Optical 200 BP25, is interposed between the run-off fluid in the cuvette 121 and photodiode 125, and absorbs or filters radiation from the lamp 123 outside the spectral range of about 380-450 nanometers, which permits passage of the violet portion of the visible spectrum. The violet spectral components passed by filter 127 are absorbed (or not) by the run-off or decolorizing fluid in the cuvette 121 and the total passed radiation impinges on the photodiode 125. The use of filter 127 reduces the number of wavelengths of radiation impinging on photodetector 125 and reduces the likelihood of error in the detection of the amount of radiation passing through the run-off fluid, which is indicative of the level of decolorization.

The electrical signal output of photodiode 125, which is proportional to the level of decolorization of the slide, is routed through an Analog Devices AD976AAN analog-to-digital converter 131. The digital output of converter then is input to the computer for analysis by a comparison routine. The comparison routine may compare the output of the photodiode to a discrete, empirically determined threshold, or may use a variety of conventional, but more sophisticated, analysis techniques to determine whether the stained sample is appropriately decolorized or whether more decolorization (acid alcohol rinse) is warranted. The PC can display various information about the staining process, including process fluid levels, number of slides processed, decolorization level, calibration data, and the like. The above-described embodiment is by way of example of a staining apparatus according to the present invention for Gram staining, it is not intended to be limiting of the invention.

The present invention provides a number of advantages. Primarily, it permits automation of the preparation of stained slides when the staining process involves decolorization, as do many slide staining procedures, including the Gram Stain. The method and apparatus according to the present invention are sufficiently simple to be reliable and relatively inexpensive to produce.

The invention has been described with reference to a preferred embodiment thereof. It is thus not limited, but is susceptible to variation and modification without departing from the scope of the claims.

The invention claimed is:

1. Apparatus for staining and analyzing a biological specimen comprising:
    a substrate carrier for removably securing a substrate having the specimen mounted thereon;
    a plurality of fluid reservoirs for storage and delivery of a plurality of fluids to the substrate, the fluids including a staining fluid and a decolorizing fluid;
    a collector for collecting run-off decolorizing fluid that runs off the substrate and specimen;
    a source of radiation arranged to irradiate the run-off decolorization fluid in the collector with radiation of a selected wavelength corresponding to the spectral color of the staining fluid;
    a photodetector for measuring a characteristic of the radiation passing through the decolorization fluid; and
    a computer configured to compare the characteristic to a selected threshold value indicative of a selected decolorization level in the biological specimen.

2. Apparatus according to claim 1, wherein the staining fluid is Gram's iodine.

3. Apparatus according to claim 1, wherein the decolorizing fluid is acid alcohol.

4. Apparatus for analyzing a biological specimen secured to a substrate, the apparatus comprising:
    a substrate carrier for securing the substrate having the specimen mounted thereon;
    a plurality of fluid reservoirs for storage and delivery of a plurality of fluids to the substrate, the fluids including a staining fluid and a decolorizing fluid;
    a source of radiation arranged to irradiate the run-off decolorizing fluid that runs off the specimen;
    a photodetector for measuring a characteristic of the radiation passing through the run-off fluid, the characteristic being indicative of a level of staining of the biological specimen;
    a wavelength-selective filter between the source of radiation and the photodetector, the wavelength selective filter configured to absorb radiation outside the spectra corresponding to the color of the staining fluid; and
    computer coupled to the photodetector and configured to detect the level of staining in the biological specimen and for indicating when the staining of the biological specimen is adequate for further analysis.

5. Apparatus according to claim 4, wherein the staining fluid is Gram's iodine.

6. Apparatus according to claim 4, wherein the decolorization fluid is acid alcohol.

7. Apparatus according to claim 4, wherein the computer includes a comparator to compare the characteristic to a selected threshold value indicative of a selected decolorization level in the biological specimen.

8. Apparatus for analyzing a biological specimen on a microscope slide, the apparatus comprising:
    a slide carrier for removably securing the slide;
    a plurality of fluid reservoirs for storage and delivery of a plurality of fluids to the specimen on the slide, the fluids including a staining fluid and a decolorizing fluid; and
    a detector configured to detect a level of staining in the biological specimen and for indicating when the staining of the biological specimen is adequate for further analysis, the detector including:
        a radiation source for irradiating the decolorizing fluid with radiation of a selected wavelength range corresponding to the spectral color of the staining fluid; and
        a photodetector for measuring a characteristic of the radiation passing through the fluid, the characteristic being indicative of a level of decolorization in the specimen.

9. Apparatus according to claim 8 wherein the detector further comprises:
    a collector for collecting run-off decolorizing fluid that runs off the substrate and biological specimen, the collector being arranged between the radiation source and the photodetector; and
    a wavelength-selective filter between the source of radiation and the photodetector, the wavelength selective filter configured to absorb radiation outside the spectra corresponding to the color of the staining fluid.

10. Apparatus according to claim 8, wherein the staining fluid is Gram's iodine.

11. Apparatus according to claim 9, wherein the decolorization fluid is acid alcohol.

12. Apparatus according to claim 8, wherein the detector compares the characteristic to a threshold value.

13. Apparatus according to claim 12, wherein the detector includes an electronic comparator to compare the characteristic to the threshold value.

* * * * *